United States Patent
Peck

(10) Patent No.: US 9,427,144 B2
(45) Date of Patent: Aug. 30, 2016

(54) METHODS AND SYSTEMS FOR DETECTING OPHTHALMIC DISEASE

(71) Applicant: Brian Peck, Clinton, IA (US)

(72) Inventor: Brian Peck, Clinton, IA (US)

(73) Assignee: Ophthalmx LLC, Clinton, IA (US)

( * ) Notice: Subject to any disclaimer, the term of this patent is extended or adjusted under 35 U.S.C. 154(b) by 0 days.

(21) Appl. No.: 14/589,778

(22) Filed: Jan. 5, 2015

(65) Prior Publication Data

US 2015/0190045 A1 Jul. 9, 2015

Related U.S. Application Data

(60) Provisional application No. 61/923,280, filed on Jan. 3, 2014.

(51) Int. Cl.
*A61B 3/14* (2006.01)
*A61B 3/00* (2006.01)
*A61B 3/11* (2006.01)

(52) U.S. Cl.
CPC ............ *A61B 3/0025* (2013.01); *A61B 3/112* (2013.01)

(58) Field of Classification Search
CPC .................... A61B 3/11; A61B 3/112
USPC ......................... 351/246, 206, 220
See application file for complete search history.

(56) References Cited

U.S. PATENT DOCUMENTS

2006/0215113 A1* 9/2006 Chernyak ............... A61B 3/11
351/246

* cited by examiner

*Primary Examiner* — Hung Dang
(74) *Attorney, Agent, or Firm* — Barnes & Thornburg LLP; Alice O. Martin

(57) ABSTRACT

Described herein are methods and systems for detecting anisocoria and evaluating an underlying disease causing anisocoria.

16 Claims, 5 Drawing Sheets

METHODS AND SYSTEMS FOR DETECTING OPHTHALMIC DISEASE

CROSS REFERENCE TO RELATED APPLICATIONS

This application also claims the benefit of provisional patent application, Ser. No. 61/923,280 filed Jan. 3, 2014 the contents of which is incorporated herein by reference thereto.

BACKGROUND

The pupil is the circular orifice in the center of the iris in the eye. Light rays enter the eye through the pupil and travel to the retina, which is the light sensitive membrane at the posterior of the eye. Changes in pupil size can be an indicator of disease. Unequal pupil sizes can also be an indicator of disease. About twenty percent of the population has anisocoria, which is a condition where pupil sizes are unequal. For the other eighty percent of the population, unequal pupil size would be an indicator of disease that can be measured and acted upon in various clinical settings.

SUMMARY

Described herein are methods and systems for detecting anisocoria and evaluating an underlying disease causing anisocoria.

DETAILED DESCRIPTION

Definitions

Figure 1:
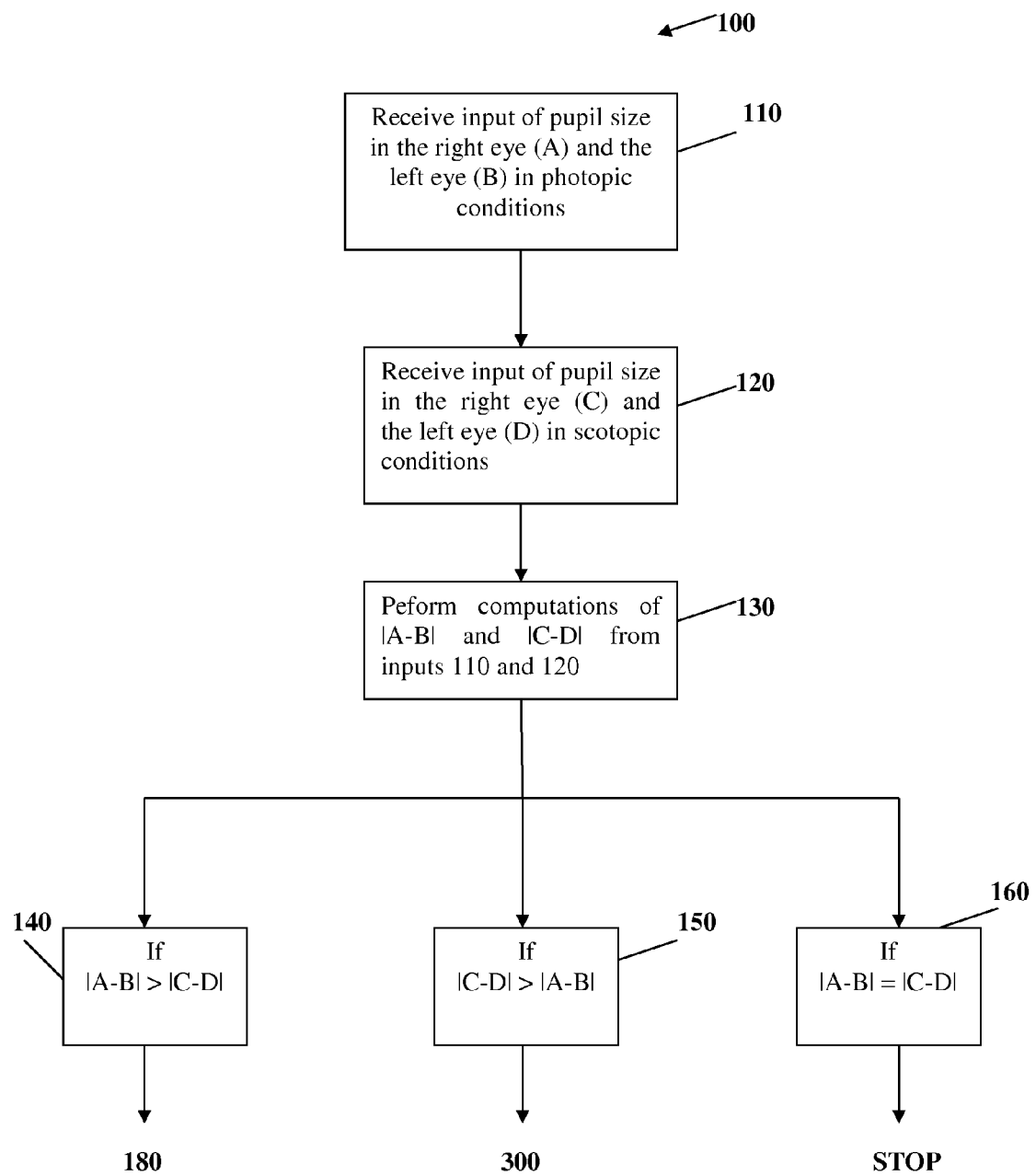
FIG. 1 is a flow chart illustrating an example method of computing pupil size to assess anisocoria.

The term "$3^{rd}$ nerve palsy" refers to palsy caused by damage to the third cranial (also named the occulomotor) nerve.

The term "Adie's tonic pupil" refers to a dilated, poorly reactive pupil, presumably from dysfunction of the ciliary ganglion behind the eye. The cause of Adie's tonic pupil is unknown. There is typically no association with underlying diseases of the eye, nerves or brain, with the exception of Adie's syndrome. In Adie's syndrome, the deep tendon reflexes may be decreased.

The term "anisocoria" refers to a condition in which the two pupils are not of equal size. "Essential", "physiologic", or "simple" anisocoria is a benign inequality of pupil size that may change over time (even hour to hour) and occurs in about 20% of the population.

The term "differential diagnosis" refers to a diagnostic decision between healthy and different disease states, including various stages of a specific disease. A subject is diagnosed as healthy or to be suffering from a specific disease, or a specific stage of a disease based on a set of hypotheses that allow for the distinction between healthy and one or more stages of the disease. A choice between healthy and one or more stages of disease depends on a significant difference between each hypothesis. Under the same principle, a "differential diagnosis" may also refer to a diagnostic decision between one disease type as compared to another.

The terms "Horner syndrome" or "oculosympathetic paresis" refer to a disorder caused by any interruption to a set of sympathetic nerve fibers that start in the hypothalamus and travel to the face and eyes. Horner syndrome is a sign of another underlying medical condition, such as a stroke, tumor, or spinal cord injury. In some cases, Homer syndrome is idiopathic. Horner syndrome usually affects only one side of the face. Typical symptoms of Horner syndrome include a drooping eyelid, decreased pupil size, and decreased sweating on the affected side of the face. Rarely, Homer syndrome can be a congenital disorder.

The term "photopic conditions" refers to bright light and/or well-lit conditions (i.e., day light). Vision under photopic conditions is mediated by cone cells of the retina.

The term "pilocarpine test" refers to the administration of 0.125% pilocarpine to an abnormally large pupil in the absence of iris sphincter damage or cranial nerve three palsy. If the pupil contracts then a diagnosis of Adie's Tonic Pupil can be made. If the pupil does not contract, 1% pilocarpine is administered to help distinguish between a cranial nerve three palsy and pharmacologically dilated pupil.

The term "pupil" refers to the circular orifice in the center of the iris, through which light rays enter the eye.

The term "scotopic conditions" refer to conditions of low light. In these conditions of low illumination, the eye must adapt to the dark conditions.

The term "slit lamp exam" refers to an evaluation of the anterior structures of the eye. Viewing of the eye is performed through a low-power microscope combined with a high-intensity light source that can be focused to shine in a thin beam.

Exemplary Methods and Systems for Performing Same

FIG. 1 is a flow chart illustrating an example method 100 of diagnosing a patient. In an example embodiment, method 100 includes operations 110, 120, 130, and 140 or 150. The methods disclosed herein utilize computing functions to diagnose a patient. The methods disclosed herein can solve a problem arising from the realm of computer technology. The methods, and more particularly the operations, disclosed herein specify how interactions with the internet are manipulated to yield a diagnosis from an observation of aniscoria.

Operation 110 and 120 is the input of pupil size measurement of a patient. Specifically, operation 110 is the input of pupil size measurements (e.g., in millimeters) of the right eye (A) and the left eye (B) in a well lit condition (photopic condition). Operation 120 is the input of pupil size measurements (e.g., in millimeters) of the right eye (C) and the left eye (D) in a dark condition (scotopic condition).

In an embodiment, operation 130 includes calculating the absolute value of the pupil size of the right eye minus the pupil size of the left eye under photopic conditions ("the photopic score"). Operation 130 can also include calculating the absolute value of the pupil size of the left eye subtracted from the pupil size of the right eye under scotopic conditions ("the scotopic score").

In an embodiment, operation 140 occurs when the result of operation 130 indicates that the absolute value of A minus B (|A-B|) is greater than the absolute value of C minus D (|C-D|) and then proceeds to operation 200. Operation 140 occurs if the absolute value of the difference between the two pupils in photopic conditions is greater than the absolute value of the difference between the two pupils in scotopic conditions.

In an embodiment, operation 150 occurs when the result of operation 130 indicates that the absolute value of C minus D (|C-D|) is greater than the absolute value of A minus B (|A-B|) and then proceeds to operation 300. Operation 140 occurs if the absolute value of the difference between the two pupils in photopic conditions is greater than the absolute value of the difference between the two pupils in scotopic conditions.

In some illustrative embodiments, operation 110 and/or operation 120 includes measuring a subject's pupil size (i.e., diameter), or otherwise determining a subject's blood pressure (such as by retrieving it from the patient's medical record or receiving it from a pupil measurement device). In some embodiments, a pupil is measured using a pupil measurement device, such as a pupilometer. In some embodiments, a medical professional measures a pupil with a pupillary distance (pd) ruler, which can be held to the eye with the medical professional's hand resting on a patient's cheek. The pd ruler is typically about 15 centimeters long with 1 mm graduations, and the millimeter graduations can be lined up along the horizontal axis starting at one edge of the pupil. A measurement can be performed by counting the number of graduations from edge to edge (diameter) of a patient's pupil. In some embodiments, a pupil measurement device is a digital device, such as including a processing device and a memory device. Some embodiments further include a data communication device configured to communicate digital data to another computing device. Some embodiments include at least one processing device and at least one memory device. Some embodiments include programmable electronics including at least one processing and at least one memory device.

After a pupil has been measured, operation 130 determines whether a subject has anisocoria. If the absolute value of (A-B) is greater than the absolute value of (C-D) 140, then operation 140 proceeds to operation 180. If the absolute value of (A-B) is less than the absolute value of (C-D) 150, then operation 150 proceeds to operation 300. If the absolute value of (A-B) is equal to the absolute value of (C-D) 160, then the operation ends.

Figure 2:
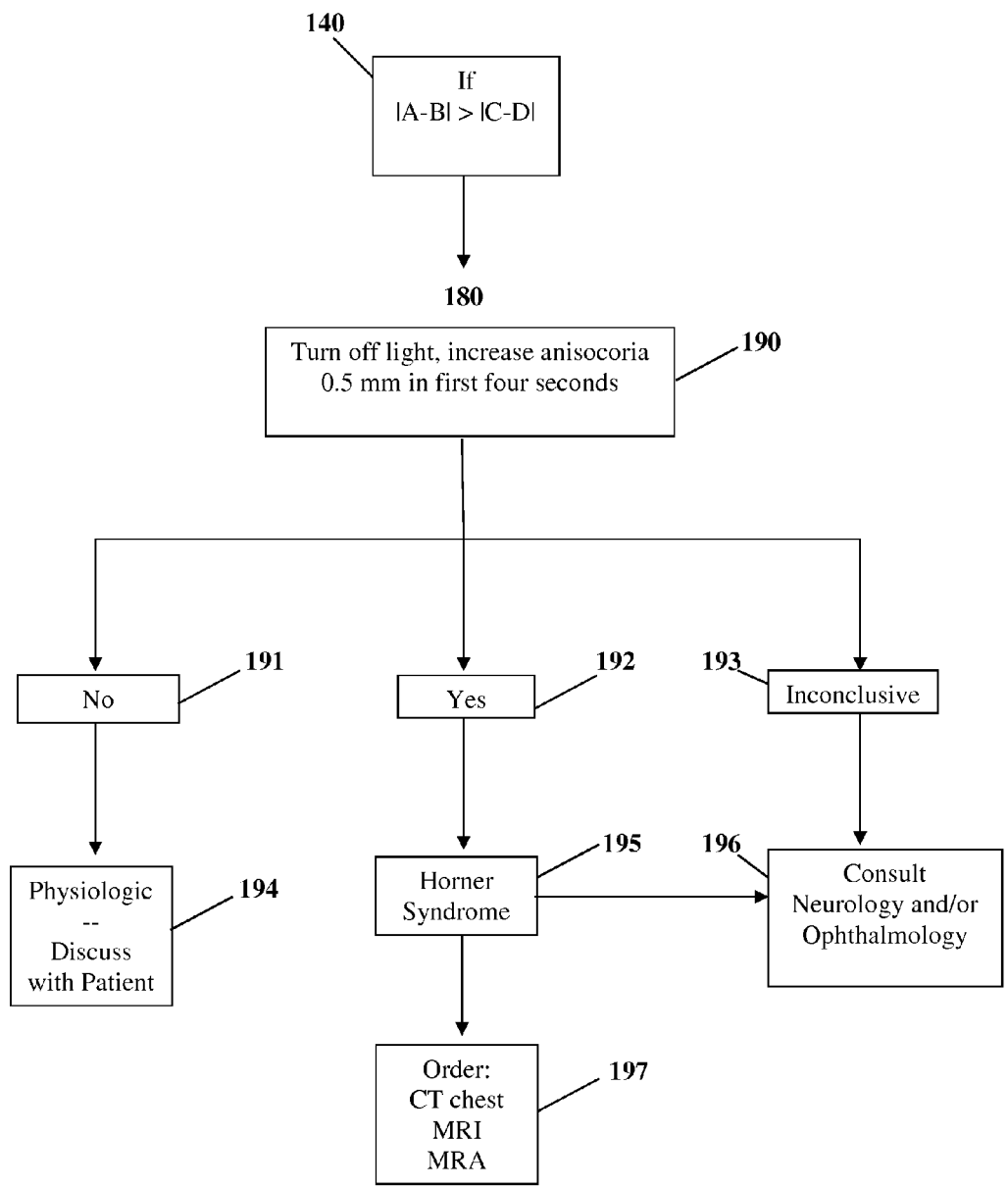
FIG. 2 is a flow chart illustrating an example method of assessing conditions associated with anisocoria in photopic conditions.

FIG. 2 is a flow chart illustrating an example method 180 of diagnosing a patient with anisocoria in photopic conditions 140.

Operation 190 directs a user to turn off all light sources and test pupil size. In particular, user is to measure whether a subject's anisocoria increases by at least 0.5 mm in the first four seconds of darkness. In an embodiment, operation 191 includes entering a determination that a subjects's anisocoria did not increase by at least 0.5 mm in the first four seconds of darkness. Following operation 191, operation 194 concludes that the anisocoria is physiologic and directs user to discuss such implications with the subject.

In an embodiment, operation 190 includes entering a determination that a subjects's anisocoria increased by at least 0.5 mm in the first four seconds of darkness. Following operation 192, operation 194 concludes that the anisocoria is due to Horner syndrome. In an embodiment, operation 195 proceeds to operation 197 allowing user to input physician orders for computed tomography (CT), magnetic resonance imaging (MRI), magnetic resonance angiogram (MRA), and combinations thereof for the subject. Operation 197 can be in communication with other databases thereby allowing direct input into an electronic medical record. Operation 197 can be in communication with another network to allow scheduling and/or orders to be placed directly with a facility conducting CT, MRI, and/or MRA. In an embodiment, operation 197 proceeds to operation 196 to consult with a neurologist and/or an ophthalmologist. In an embodiment, operation 196 is in communication with another network. In an embodiment, operation 196 interfaces with another network requesting contact from a neurologist and/or ophthalmologist. In an embodiment, operation 196 optionally includes sending the results of operation 195, and operation 193, to a neurologist and/or ophthalmologist.

Figure 3:
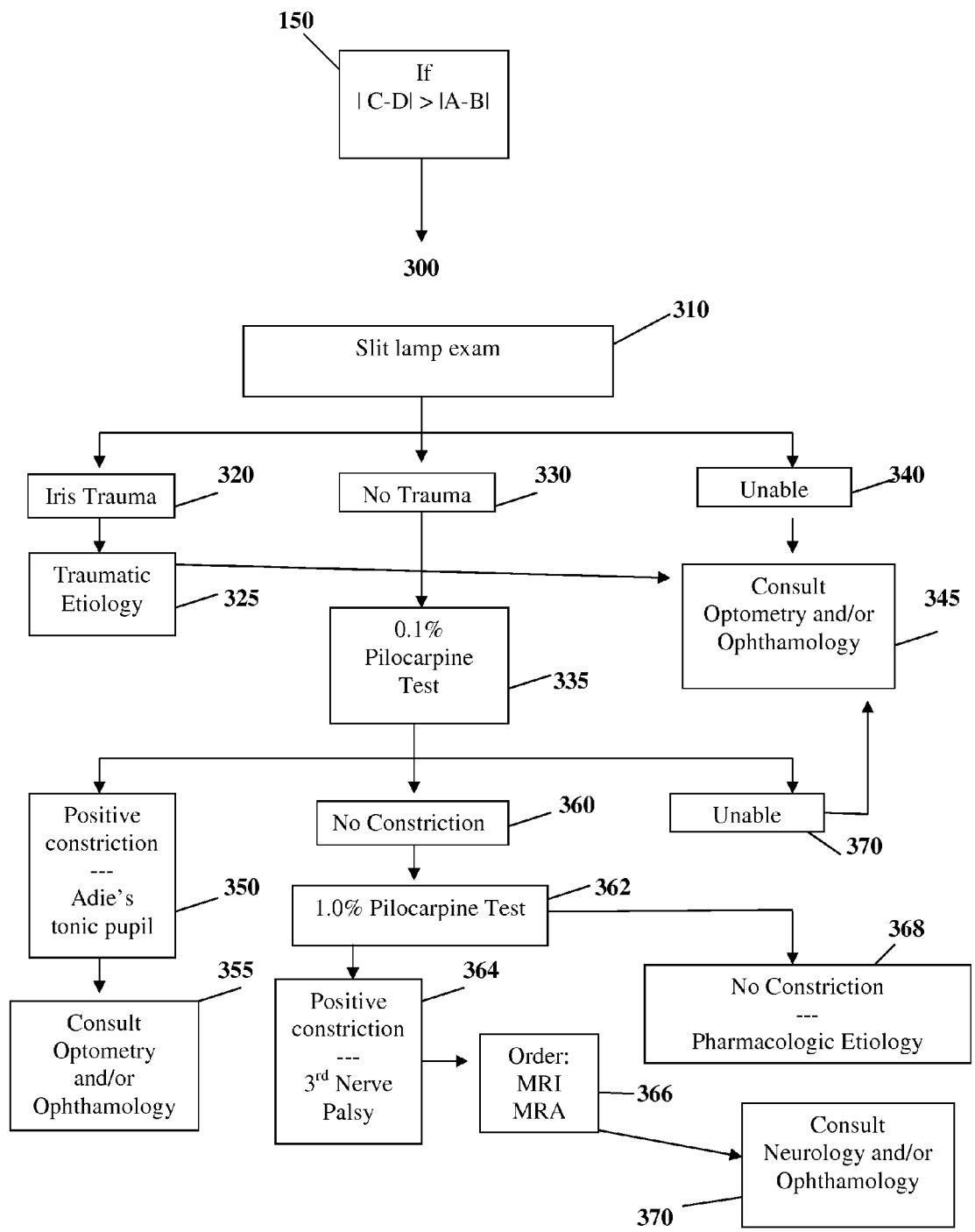
FIG. 3 is a flow chart illustrating an example method of assessing conditions associated with anisocoria in scotopic conditions.

FIG. 3 is a flow chart illustrating an example method 300 of diagnosing a patient with anisocoria in scotopic conditions 150. In an example embodiment, method 300 includes operations 320 and 325. In an example embodiment, method 300 includes operations 340 and 345. In an example embodiment, method 300 includes operations 330, 335, 350, and 355. In an example embodiment, method 300 includes operations 330, 335, 370, and optionally 345. In an example embodiment, method 300 includes operations 330, 335, 360, 362, 364, and 368.

Operation 310 directs a user to test a subject with a slit lamp exam. The slit lamp exam uses low power microscope to provide a magnified, three-dimensional (3-D) view of different parts of the eye. During the exam, your doctor can look at the front parts of the eye, including the cornea, the lens, the iris, and the vitreous humor. Optionally, eyedrops (e.g., eyedrops containing fluorescein) may be used during examination to detect trauma.

In an embodiment, trauma to the iris is detected 320 during the slit lamp examination 310. Trauma includes, but is not limited to, a laceration, a foreign object in the eye, etc. In an embodiment, operation 325 proceeds to operation 345 to consult with an ophthalmologist and/or an optometrist. In an embodiment, operation 325 is in communication with another network. In an embodiment, operation 325 interfaces with another network requesting contact from an ophthalmologist and/or an optometrist. In an embodiment, operation 325 optionally includes sending the results of operation 325 to an ophthalmologist and/or an optometrist.

In an embodiment, the slit lamp exam does not provide a definitive answer to whether there is trauma in the eye. In an embodiment, operation 340 proceeds to operation 345 to consult with an ophthalmologist and/or an optometrist. In an embodiment, operation 340 is in communication with another network. In an embodiment, operation 340 interfaces with another network requesting contact from an ophthalmologist and/or an optometrist. In an embodiment, operation 340 optionally includes sending the results of operation 340 to an ophthalmologist and/or an optometrist.

In an embodiment, operation 330 is the input of "no trauma" in response to operation 310. Follwing the input of "no trauma" 330, method 300 continues to operation 335 prompting user to administer a 0.1% pilocarpine test 335. Pilocarpine is a cholinergic agonist used to stimulate parasympathomimetic reactions by responsive tissues. Pilocarpine can be administered as an ophthalmic solution (e.g., eye drops), such as pilocarpine hydrochloride or pilocarpine nitrate. Input of positive constriction following administration of 0.1% pilocarpine 350 indicates Adie's tonic pupil. In an embodiment, operation 350 proceeds to operation 355 to consult with an ophthalmologist and/or an optometrist. In an embodiment, operation 350 is in communication with another network. In an embodiment, operation 350 interfaces with another network requesting contact from an ophthalmologist and/or an optometrist. In an embodiment, operation 350 optionally includes sending the results of operation 350 to an ophthalmologist and/or an optometrist in operation 355.

In an embodiment, the 0.1% pilocarpine test cannot be administered to a subject. A pilocarpine test can be contraindicated due to hypersensitivity to one or more components of the ophthalmic solution, acute iritis, or pupillary block glaucoma. If the pilocarpine test 335 is unable to be administered or produces uninterpretable results (operation 370), then operation 370 proceeds to operation 345 to consult with an ophthalmologist and/or an optometrist. In an embodiment, operation 370 is in communication with another network. In an embodiment, operation 370 interfaces with another network requesting contact from an ophthalmologist and/or an optometrist. In an embodiment, operation 370 optionally includes sending the results of operation 370 to an ophthalmologist and/or an optometrist.

In an embodiment, administration of 0.1% pilocarpine to a subject produces no constriction of the pupil. Operation 360 is the input of no constriction. Operation 362 prompts administration of 1.0% pilocarpine. Input of constriction 364 of the pupil following the administration of 1.0% pilocarpine indicates $3^{rd}$ nerve palsy. To further assess a subject's $3^{rd}$ nerve palsy, operation 364 to operation 366 allowing user to input physician orders for computed magnetic resonance imaging (MRI) and/or magnetic resonance angiogram (MRA) for a subject. Operation 366 can be in communication with other databases thereby allowing direct input into an electronic medical record. Operation 366 can be in communication with another network to allow scheduling and/or orders to be placed directly with a facility conducting an MRI and/or MRA. In an embodiment, operation 366 proceeds to operation 370 to consult with a neurologist and/or an ophthalmologist. In an embodiment, operation 370 is in communication with another network. In an embodiment, operation 370 interfaces with another network requesting contact from a neurologist and/or ophthalmologist. In an embodiment, operation 370 optionally includes sending the results of operation 330, operation 360, operation 364, or combinations thereof to a neurologist and/or ophthalmologist.

In an embodiment, operation 368 is the input of no constriction. No constriction after the administration of 1.0% pilocarpine indicates a pharmacologic etiology of anisocoria. Examples of etiologic agents that can cause anisocoria under these conditions include, but are not limited to pharmacological pupil dilation. Operation 368 lists pharmacologic agents and combinations thereof (not shown) to query a subject as to a cause of the anisocoria. An embodiment, allows input for "yes" or "no" for whether the subject has been administered the pharmacologic agents and combinations thereof. Operation 368 can be in communication with other databases thereby allowing direct input into an electronic medical record.

Figure 4:
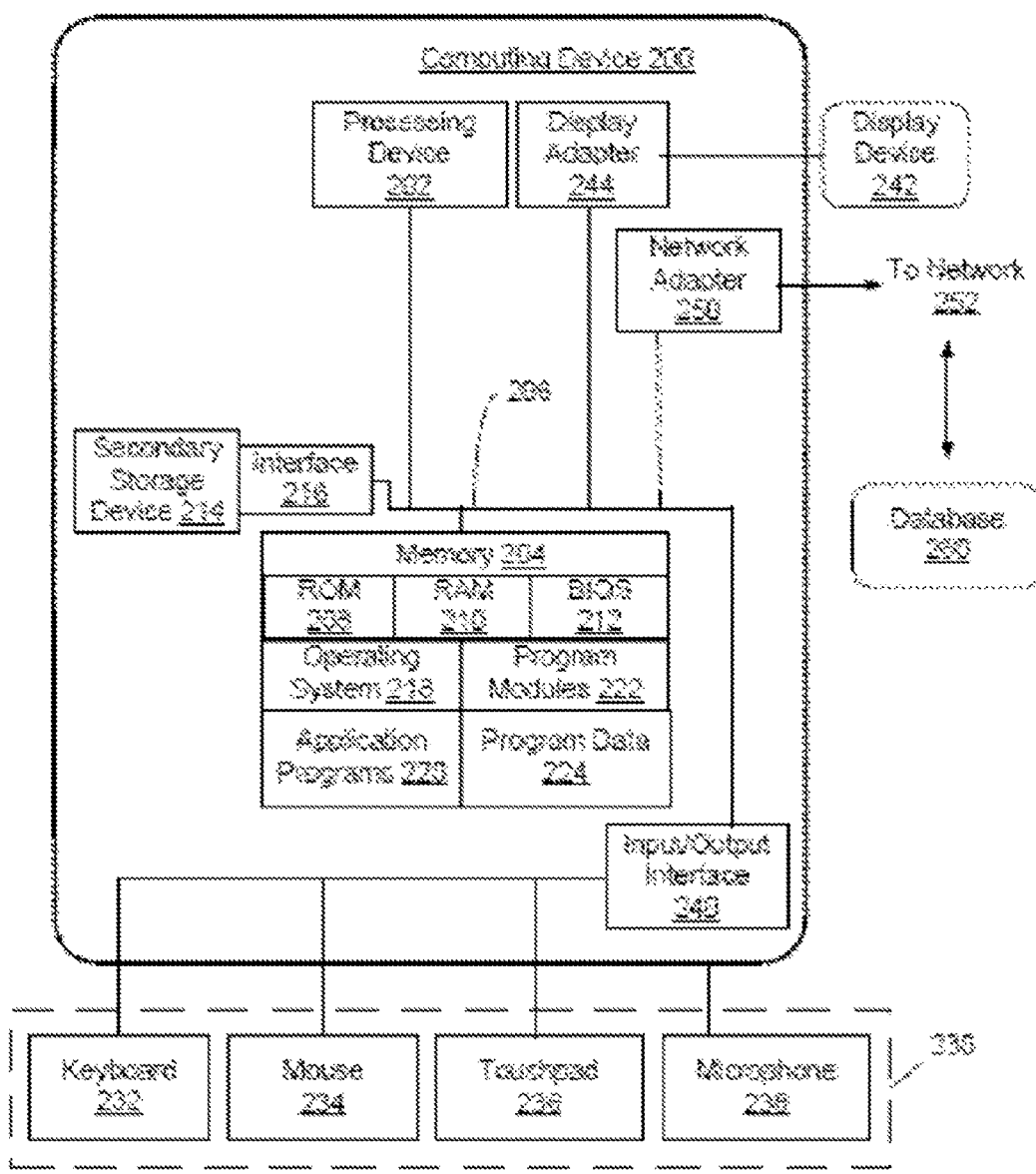
FIG. 4 is a schematic block diagram illustrating an architecture of an example computing device for implementing various aspects according to embodiments disclosed herein.
Figure 4:
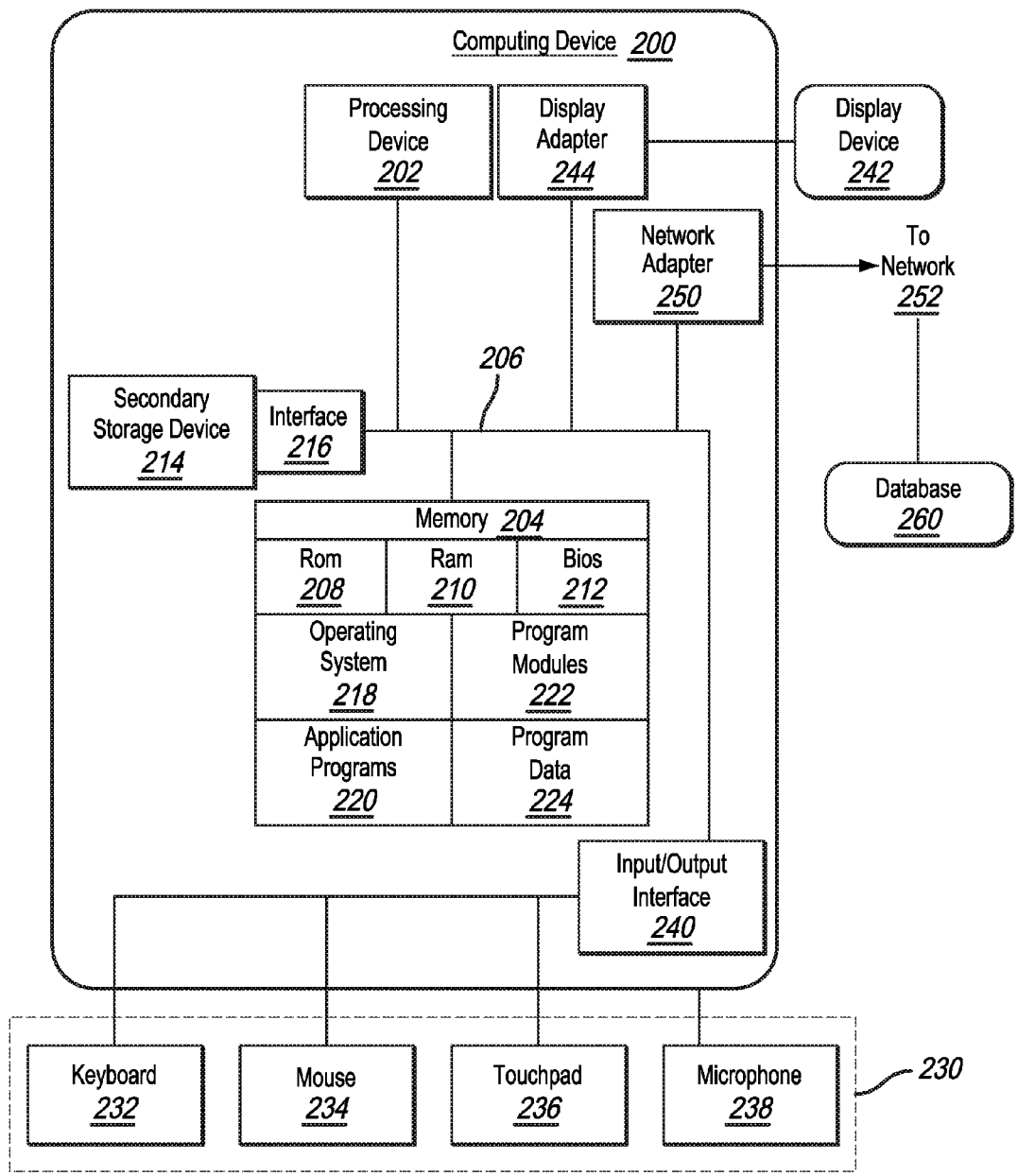

FIG. 4 is a schematic block diagram illustrating an architecture of an example computing device 200 for implementing various aspects according to the present disclosure. The computing device 200 can be used to perform some or all of one or more of the methods, operations, computations, or processes discussed herein, such as those illustrated and described herein with reference to FIGS. 1-3. In addition, some embodiments include two or more computing devices that operate together to perform aspects disclosed herein.

In one example, a computing device 200 is a personal computer. Other embodiments include other computing devices 200, such as a tablet computer, a smart phone, a personal digital assistant (PDA), or other device configured to process data instructions. In some embodiments, computing device 200 is an example of programmable electronics. In another possible embodiment, two or more computing devices 200 collectively form at least a portion of the programmable electronics. In another embodiment, a medical device (e.g., a pupilometer) may have a computing component and thus also be a computing device to measure pupil size and send the measurements as inputs into 110 and 120.

A computing device 200 includes, in some embodiments, at least one processing device 202 and memory 204. A variety of processing devices 202 are available from a variety of manufacturers, for example, Intel or Advanced Micro Devices. In some embodiments, a processing device 202 is configured to perform one or more methods or operations as defined by instructions stored in a memory device. Examples of such methods and operations are described herein.

A computing device 200 also includes, in some embodiments, at least one memory device 204. Examples of memory devices 204 include read-only memory 208 and random access memory 210. Basic input/output system 212, containing basic routines that act to transfer information within computing device 200, such as during start up, is typically stored in read-only memory 208. Memory device 204 can be a part of processing device 202 or can be separate from processing device 202.

In this example, a computing device 200 also includes system bus 206 that couples various system components including memory 204 to processing device 202. System bus 206 is one of any number of types of bus structures including a memory bus, or memory controller; a peripheral bus; and a local bus using any of a variety of bus architectures.

In some embodiments, a computing device 200 also includes secondary storage device 214 for storing digital data. An example of a secondary storage device is a hard disk drive. Secondary storage device 214 is connected to system bus 206 by secondary storage interface 216. Secondary storage devices 214 and their associated computer readable media provide nonvolatile storage of computer readable instructions (including application programs and program modules), data structures, and other data for computing device 200.

Although the exemplary architecture described herein employs a hard disk drive as a secondary storage device, other types of computer readable media are included in other embodiments. Examples of these other types of computer readable media include magnetic cassettes, flash memory cards, digital video disks, Bernoulli cartridges, compact disc read only memories, digital versatile disk read only memories, random access memories, read only memories, or other memory devices.

A number of program modules can be stored in secondary storage device 214 or memory 204, including operating system 218, one or more application programs 220, other program modules 222, and program data 224. In some embodiments, program modules include data instructions that are stored in computer readable media (such as computer readable storage media). When data instructions are executed by a processing device 202, the processing device 202 performs one or more methods or operations described herein.

In some embodiments, a user provides inputs to a computing device 200 through one or more input devices 230. Examples of input devices 230 include a keyboard 232, mouse 234, touchpad 236 (or a touch sensitive display), and microphone 238. Other embodiments include other input devices 230. Input devices 230 are often connected to the processing device 202 through an input/output interface 240 that is coupled to system bus 206. These input devices 230 can be connected by any number of input/output interfaces, such as a parallel port, serial port, game port, or a universal serial bus. Wireless communication between input devices and interface 240 is possible as well, and includes infrared, Bluetooth® wireless technology, 802.11a/b/g/n/z wireless communication, cellular communication, or other radio frequency communication systems in some possible embodiments.

In some embodiments, a display device 242, such as a monitor, liquid crystal display device, projector, or touch screen display device, is also connected to system bus 206 via an interface, such as display adapter 244. In addition to display device 242, a computing device 200 can include various other peripheral devices (not shown), such as speakers or a printer. When used in a local area networking environment or a wide area networking environment (such as the Internet), computing device 200 is typically connected to network 252 through a network interface or adapter 250. Other possible embodiments use other communication devices. For example, some embodiments of computing device 200 include a modem for communicating across network 252.

A computing device 200 typically includes at least some form of computer-readable media. Computer readable media include any available media that can be accessed by computing device 200. By way of example, computer-readable media include computer readable storage media and communication media. The term "computer readable media" as used herein includes computer storage media. Computer storage media includes volatile and nonvolatile, removable and non-removable media implemented in any method or technology for storage of information, such as computer readable instructions, data structures, program modules, or other data. Computer readable storage media include, but is not limited to, read-only memory 208, random access memory 210, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by computing device 200. In some embodiments, computer readable storage media are non-transitory media.

Communication media can be embodied by computer readable instructions, data structures, program modules or other data in a modulated data signal, such as a carrier wave or other transport mechanism and includes any information delivery media. The term "modulated data signal" refers to a signal that has one or more of its characteristics set or changed in such a manner as to encode information in the signal. By way of example, communication media include wired media such as a wired network or direct-wired connection, and wireless media such as acoustic, radio frequency, infrared, and other wireless media. In some embodiments, communication media are transitory media. Combinations of any of the above are also included within the scope of computer readable media.

A database 260 is also illustrated in FIG. 4. In some embodiments, a database is a separate device from a computing device 200, and is in data communication with the computing device 200, such as across a network 252. In another possible embodiment, however, a database 260 is a memory device that is part of a computing device 200. In some embodiments, a database 260 includes a medical records database. In another embodiment, a database 260 includes subject data, such as the compilation of data for a plurality of subjects. Data can include, for example, one or more of the following for each subject: pupil size, pupil size under photopic conditions, pupil size under scotopic conditions, neurological disorders, and ophthalmic disorders.

The invention claimed is:

1. A method of analyzing anisocoria in a subject comprising:
receiving with programmable electronics a first input identifying pupil size of the subject in photopic conditions; receiving with the programmable electronics a second input identifying pupil size of the subject in scotopic conditions; and computing with the programmable electronics a photopic score and a scotopic score using the first and second pupil size inputs of the subject and storing the scores in a memory device.

2. The method of claim 1, further comprising determining if the subject has anisocoria.

3. The method of claim 2, further comprising: determining whether anisocoria increases by at least 0.5 mm in first four seconds of scotopic conditions.

4. The method of claim 3, further comprising prompting only if determined that the subject has amscona.

5. The method of claim 2 further defined as determining results whether the absolute value of the pupil size of the right eye in photopic conditions minus the absolute value of the pupil size of the left eye in photopic condition, is greater than, equal to, or less than, the absolute value of the pupil size in the right eye in scotopic conditions minus the absolute value of the pupil size in the left eye in scotopic condition, and wherein further diagnosis and/or treatment strategies are selected based on these results, as in FIGS. 1, 2 and 3.

6. The method of claim 1, wherein the programmable electronics include at least one processor and the least one memory device.

7. The method of claim 6, wherein the programmable electronics include at least two processors.

8. The method of claim 7 wherein the at least two processors are in data communication across a data communication network.

9. The method of claim 1, wherein receiving the first and second inputs comprises receiving the first and second inputs with an input device of a computing device.

10. The method of claim 1, further comprising displaying the standard score on a display device of the programmable electronics, wherein the programmable electronics include a computing device.

11. The method of claim 1, further comprising saving the scotopic and photopic scores in a medical record of a subject in a medical records database.

12. The method of claim 1, further comprising sending the photopic and scotopic scores to a computing device across a network.

13. A computer-readable storage medium comprising instructions that, when executed by a computer, cause the computer to: receive a first input identifying a pupil size of a subject under photopic conditions; receive a second input identifying a pupil size of a subject under scotopic conditions; and compute with a computing device photopic and scotoic scores using the first and second inputs of the subject and storing the scores in a memory device.

14. The computer-readable storage medium of claim 13, wherein the first input is received with the computing device with an input device.

15. The computer-readable storage medium of claim 13, wherein the first input is received from a second computing device.

16. A system comprising: at least one processor; and memory, the memory storing instructions that, when executed by the processor, cause the processor to: receive a first input identifying a pupil size of a subject under photopic conditions; receive a second input identifying a pupil size of a subject under scotopic conditions; and compute with a computing device a photopic score and a scotopic score using the first and second inputs of the subject and storing the scores in a memory device.

* * * * *